United States Patent [19]    [11] Patent Number: 5,637,467
Meltzer                        [45] Date of Patent:  Jun. 10, 1997

[54] HETEROGENEOUS ASSAY USING A PENDULOUS DROP

[75] Inventor: Robert J. Meltzer, Kirkland, Wash.

[73] Assignee: Behringwerke AG, Marburg, Germany

[21] Appl. No.: 412,636

[22] Filed: Mar. 29, 1995

Related U.S. Application Data

[63] Continuation of Ser. No. 960,032, Oct. 13, 1992, abandoned.

[51] Int. Cl.[6] ..................................... G01N 33/53
[52] U.S. Cl. .................. 435/7.9; 435/7.93; 435/7.94; 435/188; 436/528; 436/545; 436/546; 436/164; 436/172; 436/810
[58] Field of Search ..................... 435/6, 7.9, 7.93, 435/7.94, 188; 436/528, 546, 164, 172, 810

[56] References Cited

U.S. PATENT DOCUMENTS

| | | | |
|---|---|---|---|
| Re. 31,006 | 8/1982 | Schuurs et al. | 435/7 |
| 3,654,090 | 4/1972 | Schuurs et al. | 195/103.5 |
| 3,839,153 | 10/1974 | Schuurs et al. | 195/103.5 R |
| 3,850,752 | 11/1974 | Schuur et al. | 195/103.5 R |
| 4,016,043 | 4/1977 | Schuurs et al. | 195/103.5 R |
| 4,116,638 | 9/1978 | Kenoff | 422/99 |
| 4,447,546 | 5/1984 | Hirschfeld | 436/527 |
| 4,454,235 | 6/1984 | Johnson | 436/536 |
| 4,590,157 | 5/1986 | Chandler et al. | 435/7 |
| 4,690,907 | 9/1987 | Hibino et al. | 436/514 |
| 4,844,869 | 7/1989 | Glass | 422/68 |
| 4,883,760 | 11/1989 | Heelies | 435/296 |
| 4,918,025 | 4/1990 | Greaner | 436/165 |
| 5,110,431 | 5/1992 | Moring | 104/180.1 |
| 5,110,724 | 5/1992 | Hewett | 435/11 |
| 5,164,294 | 11/1992 | Skold et al. | 435/7.5 |

FOREIGN PATENT DOCUMENTS

| | | |
|---|---|---|
| 0160900 | 11/1985 | European Pat. Off. |
| 2084317 | 4/1982 | United Kingdom |

OTHER PUBLICATIONS

Shekarchi, I.C. et al. J. Clin Microbiol. 25(2):320 Feb. 1987.
Healey, K. et al Clin Chim Acta 134:51 1983.

Primary Examiner—James C. Housel
Assistant Examiner—Theresa King
Attorney, Agent, or Firm—Shelley G. Precivale; Janet K. Kaku; Pauline Ann Clarke

[57] ABSTRACT

As method of determining an analyte is described, where a medium suspected of containing an analyte is drawn into a capillary tube by capillary action, such that if the analyte is present, it becomes immobilized in the tube. This medium is expelled from the tube and, optionally, one or more additional reagents are similarly drawn up and expelled. When the last fluid is expelled from the tube, a pendulous drop is caused to form at the opening of the capillary tube and is examined for the presence or intensity of the signal, which is related to the presence or amount of analyte in the medium.

55 Claims, 2 Drawing Sheets

HETEROGENEOUS ASSAY USING A PENDULOUS DROP

This is a continuation of application U.S. Ser. No. 07/960,032, filed Oct. 13, 1992 now abandoned.

BACKGROUND OF THE INVENTION

1. Field of the Invention

Heterogeneous immunoassays such as the solid phase enzyme linked immunosorbent assay (ELISA), have numerous advantages for assaying low level analytes.

Despite these advantages, present assay methods suffer from a number of difficulties. For example, the ELISA uses a relatively large volume of reagents, which impacts the cost of the assay, and also uses relatively large volumes of wash solution, which presents a disposal problem. Additionally, the washing operation itself is awkward in terms of the plumbing required.

Another disadvantage of heterogeneous assays is that, in order to produce a result in a reasonable time, a high ratio of the surface of the solid phase to the volume of reactants is required. One of the ways to achieve this high ratio has been the use of beads or microspheres as the solid phase. To measure the result of the assay's signal producing system requires some means of separating the liquid from the solid phase.

It is the purpose of this invention to obviate these difficulties associated with heterogenous assays such as the ELISA and other similar assay techniques.

2. Description of the Related Art

The enzyme linked immunosorbent assay (ELISA) is described in numerous patents, for example, Shuurs, et al., U.S. Pat. Nos. 3,654,090; 3,850,752; 3,839,153; 4,016,043; and Shuurs, et al., U.S. Pat. No. Re. 31,006.

Capillary tubes have been used for immunoassays in several different ways.

In one scheme, a capillary tube is used to simply transfer assay components from one cuvette to another, as in Johnson, U.S. Pat. No. 4,454,235; or to deliver a controlled volume onto an absorbent test pad, as in Hewett, U.S. Pat. No. 5,110,724.

In a more involved technique, analyte bound to the inner surface of the tube, is detected by examining the tube through its clear or transparent surface. Hibino, et al., U.S. Pat. No. 4,690,907, describes an assay where the capillary tube is divided into several zones, with each zone containing a different assay reagent. Heelies, U.S. Pat. No. 4,883,760, discloses an immunoassay where sample and assay reagents are added to the top of a reagent-coated tube and withdrawn by means of absorbent material positioned at the bottom of the tube. Grenner, U.S. Pat. No. 4,918,025, describes a self contained assay device where a capillary tube functions as the reaction zone.

Another technique uses an optical fiber coated with an immunoreactant that is positioned within a capillary tube to detect the presence of analyte by fluorescence, such as described in Hirschfeld, U.S. Pat. No. 4,447,546 and Glass, U.S. Pat. No. 4,844,869.

Some techniques utilize a plurality of capillary tubes. In Chandler, et al., U.S. Pat. No. 4,590,157, numerous tubes are positioned in series or in sequence, each capable of binding with a different analyte so that a single sample can be screened against a number of antibodies or antigens in one test sequence. Kenoff, U.S. Pat. No. 4,116,638 describes using both the interior and exterior surfaces of a plurality of capillary tubes as the solid support for immunoassays. Morin, et al., U.S. Pat. No. 5,110,431 discloses a technique where two capillaries are aligned end to end with a small gap between them and placed in a buffer solution. Under an applied voltage a sample liquid can be coupled in the gap and tagged with a label.

SUMMARY OF THE INVENTION

This invention relates to a method of determining an analyte comprising the steps of: drawing a first medium suspected of containing an analyte into a capillary tube to capture the analyte, if present; expelling the first medium from the tube; drawing a second medium containing a labeled specific binding pair ("sbp") member into the tube if the first medium does not contain a labeled sbp member, wherein the labeled sbp member is capable of binding the analyte or a second sbp member capable of binding the analyte; expelling the second medium from the tube; drawing a third medium containing reagents for producing a signal from the label if the label is not capable of directly producing a signal; expelling the third medium from the tube; and examining a drop of the first medium or the second or third medium, if a second or third medium is used, for the presence or intensity of a signal, the presence or intensity thereof being related to the presence or amount of analyte in the first medium.

This invention also pertains to a method of determining an analyte comprising the steps of: drawing a first medium suspected of containing an analyte into a capillary tube, where the capillary tube is coated internally with a first specific binding pair ("sbp") member capable of binding the analyte, and incubating the medium and first sbp member whereby a first complex involving the analyte and the first sbp member is formed in relation to the presence of analyte in the first medium; expelling the first medium from the tube; drawing a second medium containing a labeled second sbp member into the tube, wherein the labeled second sbp member is capable of binding the analyte or a third sbp member capable of binding the analyte, and incubating the labeled second sbp member and the first complex, if present, to form a labeled complex; expelling the second medium from the tube; drawing a third medium containing reagents for producing a signal from the label if the label is not capable of directly producing a signal; expelling the third medium, if a third medium is used, from the tube; wherein the second or third medium, if used, is expelled to form a pendulous drop, and the pendulous drop is examined for the presence or intensity of a signal, the presence or intensity thereof being indicative of the presence or amount of analyte in the first medium.

This invention further relates to a method of determining an analyte comprising the steps of: drawing a first medium suspected of containing an analyte into a capillary tube, where the first medium contains a labeled analog of the analyte and where the capillary tube is coated internally with a specific binding pair ("sbp") member capable of binding the analyte and the labeled analog; expelling the first medium from the tube; drawing a second medium containing reagents for producing a signal from the label if the label is not capable of directly producing a signal; expelling the second medium, if a second medium is used, from the tube; wherein the first or second medium, if used, is expelled to form a pendulous drop, and the pendulous drop is examined for the presence or intensity of the signal, the presence or intensity thereof being indicative of the presence or amount of analyte in the first medium.

DESCRIPTION OF THE SPECIFIC EMBODIMENTS

As mentioned above, the present invention concerns a method of determining an analyte where a medium suspected of containing an analyte is drawn into a capillary tube by capillary action, such that if the analyte is present, it becomes immobilized in the tube. This medium is expelled from the tube and, optionally, one or more additional reagents are similarly drawn up and expelled. When the last fluid is expelled from the tube, a pendulous drop is caused to form at the opening of the capillary tube. This pendulous drop of fluid is then examined to detect the presence or intensity of signal, which is related to the presence or amount of analyte in the medium.

The method of this invention has several distinct advantages. The method uses a total volume of fluids less than 200 μL, assuming about 2–4 6-fold washes, where each fold wash uses a volume approximately equal to the reaction volume of the capillary. For example, five hundred samples would then produce less that a liter of waste solution. The washing operation is a straightforward flow through the capillary. The capillary tube is disposable and has a small volume, making it easily crushed and compacted after use. Lastly, the pendulous drop is an easy way to separate the measured volume from the solid phase.

Before proceeding further with a description of specific embodiments of the invention of the present invention, a number of terms will be defined.

Analyte: the compound or composition to be detected. The analyte can be a member of a specific binding pair ("sbp") and may be a ligand, which is monovalent (monoepitopic) or polyvalent (polyepitopic), usually antigenic or haptenic, and is a single compound or plurality of compounds that share at least one common epitopic or determinant site. The analyte can be a part of a cell such as bacteria or a cell bearing a blood group antigen such as A, B, D, etc., or an HLA antigen or a microorganism, e.g., bacterium, fungus, protozoan, or virus.

Polyvalent ligand analytes will normally be poly(amino acids), i.e., polypeptides and proteins, polysaccharides, nucleic acids, and combinations thereof. Such combinations include components of bacteria, viruses, chromosomes, genes, mitochondria, nuclei, cell membranes and the like. For the most part, the polyepitopic ligand analytes to which the subject invention can be applied will have a molecular weight of at least about 5,000, more usually at least about 10,000. In the poly(amino acid) category, the poly(amino acids) of interest will generally be from about 5,000 to 5,000,000 molecular weight, more usually from about 20,000 to 1,000,000 molecular weight. Among the hormones of interest, the molecular weights will usually range from about 5,000 to 60,000 molecular weight.

A wide variety of proteins may be considered as to the family of proteins having similar structural features, proteins having particular biological functions, proteins related to specific microorganisms, particularly disease causing microorganisms, etc. Such proteins include, for example, immunoglobulins, cytokines, enzymes, hormones, cancer antigens, nutritional markers, tissue specific antigens, etc.

The following are classes of proteins related by structure: protamines, histones, albumins, globulins, scleroproteins, phosphoproteins, mucoproteins, chromoproteins, lipoproteins, nucleoproteins, glycoproteins, T-cell receptors, proteoglycans, HLA, and unclassified proteins such as somatotropin, prolactin, insulin and pepsin.

A number of proteins found in the human plasma are important clinically and include: prealbumin, albumin, $\alpha_1$-lipoprotein, $\alpha_1$-antitrypsin, $\alpha_1$-glycoprotein, transcortin, 4.6S-postalbumin, tryptophan-poor $\alpha_1$-glycoprotein, $\alpha_1$X-glycoprotein, thyroxin-binding globulin, inter-$\alpha$-trypsin-inhibitor, Gc-globulin (Gc 1-1, Gc 2-1 and Gc 2-2), Haptoglobin (Hp 1-1, Hp 2-1 and Hp 2-2), ceruloplasmin, cholinesterase, $\alpha_2$-lipoprotein(s), myoglobin, C-reactive protein, $\alpha_2$-macroglobulin, $\alpha_2$-HS-glycoprotein, Zn-$\alpha_2$-glycoprotein, $\alpha_2$-neuramino-glycoprotein, erythropoietin, β-lipoprotein, transferrin, hemopexin, fibrinogen, plasminogen, $\beta_2$-glycoprotein I and $\beta_2$-glycoprotein II, Immunoglobulin G (IgG) or γG-globulin (Mol. formula: $\gamma_2\kappa_2$ or $\gamma_2\lambda_2$), Immunoglobulin A (IgA) or γA-globulin (Mol. formula: $(\alpha_2\kappa_2)^n$ or $(\alpha_2\lambda_2)^n$), Immunoglobulin M (IgM) or βM-globulin (Mol. formula: $(\mu_2\kappa_2)^5$ or $(\mu_2\lambda_2)^5$), Immunoglobulin D (IgD) or γD-Globulin (γD) (Mol. formula: $\delta_2\kappa_2$ or $\delta_2\lambda_2$), Immunoglobulin E (IgE) or γE-Globulin (γE) (Mol. formula: $\epsilon_2\kappa_2$ or $\epsilon_2\lambda_2$), free κ and λ light chains, and complement factors (C'1, including C'1q, C'1r and C'1s; C'2; C'3, including $\beta_1$A and $\alpha_2$:D; C'4; C'5; C'6; C'7; C'8; and C'9).

Important blood clotting factors (International designation) include: fibrinogen (I), prothrombin (II), thrombin (IIa), tissue thromboplastin (III), proaccelerin/accelerator globulin (V and VI), proconvertin (VII), antihemophilic globulin (VIII), Christmas factor/plasma thromboplastin component (IX), Stuart-Prower factor/autoprothrombin III (X), plasma thromboplastin antecedent (XI), Hagemann factor (XII) and fibrin-stabilizing factor (XIII).

Important protein hormones include: peptide and protein hormones such as parathyroid hormone (parathromone), thyrocalcitonin, insulin, glucagon, relaxin, erythropoietin, melanotropin (melanocyte-stimulating hormone; intermedin), somatotropin (growth hormone), corticotropin (adrenocorticotropic hormone), thyrotropin, follicle-stimulating hormone, luteinizing hormone (interstitial cell-stimulating hormone), luteomammotropic hormone (luteotropin, prolactin), gonadotropin (chorionic gonadotropin); tissue hormones such as secretin, gastrin, angiotensin I and II, bradykinin and human placental lactogen; cytokines such as IL I, IL II, IL VI, EGF, TNF and NGF; cancer antigens such as PSA, CEA, $\alpha$-fetoprotein, acid phosphatase, CA 19.9 and CA 125; tissue specific antigens such as alkaline phosphatase, myoglobin, CPK-MB, calcitonin and myelin basic protein; and peptide hormones from the neurohypophysis such as oxytocin, vasopressin, and Releasing factors (CRF, LRF, TRF, Somatotropin-RF, GRF, FSH-RF, PIF and MIF).

Other polymeric materials of interest are mucopolysaccharides and polysaccharides.

Illustrative antigenic polysaccharides derived from microorganisms are as follows:

| Species of Microorganisms | Hemosensitinin Found in |
| --- | --- |
| Streptococcus pyogenes | Polysaccharide |
| Diplococcus pneumoniae | Polysaccharide |
| Neisseria menigitidis | Polysaccharide |
| Neisseria gonorrhoeae | Polysaccharide |
| Corynebacterium diphtheriae | Polysaccharide |

-continued

| Species of Microorganisms | Hemosensitinin Found in |
|---|---|
| Actinobacillus mallei | Crude extract |
| Actinobacillus | |
| Francisella tularenis | Lipopolysaccharide, Polysaccharide |
| Pasteurella pestis | Polysaccharide |
| Pasteurella multocida | Capsular antigen |
| Brucella abortus | Crude extract |
| Haemophilus influenzae | Polysaccharide |
| Haemophilus pertussis | Crude |
| Treponema reiteri | Polysaccharide |
| Veillonella | Lipopolysaccharide |
| Erysipelothrix | Polysaccharide |
| Listeria monocytogenese | Polysaccharide |
| Chromobacterium | Lipopolysaccharide |
| Mycobacterium tuberculosis | Saline extract of 90% phenol extracted mycobacteria and polysaccharide fraction of cells and tuberculin |
| Klebsiella aerogenes | Polysaccharide |
| Klebsiella cloacae | Polysaccharide |
| Salmonella typhosa | Lipopolysaccharide, Polysaccharide |
| Salmonella typhimurium | Polysaccharide |
| Salmonella derby | |
| Salmonella pullorum | |
| Shigella dysenteriae | Polysaccharide |
| Shigella flexneri | |
| Shigella sonnei | Crude, polysaccharide |
| Rickettsiae | Crude extract |
| Candida albicans | Polysaccharide |
| Entamoeba histolytica | Crude extract |

The microorganisms that are assayed may be intact, lysed, ground or otherwise fragmented, and the resulting composition or portion, e.g. by extraction, assayed. Microorganisms of interest include:

Corynebacteria
  Corynebacterium diphtherias
Pneumococci
  Diplococcus pneumonias
Streptococci
  Streptococcus pyogenes
  Streptococcus salivarus
Staphylococci
  Staphylococcus aureus
  Staphylococcus albus
Neisseriae
  Neisseria meningitidis
  Neisseria gonorrhoea
Enterobacteriaceae
  The coliform bacteria
    Escherichia coli
    Aerobacter aerogenes
    Klebsiella pneumonias
  The Salmonellae
    Salmonella typhosa
    Salmonella choleraesuis
    Salmonella typhimurium
  The Shigellae
    Shigella dysenteriae
    Shigella schmitzii
  The Shigellae con't
    Shigella arabinotarda
    Shigellae flexneri
    Shigella boydii
    Shigella sonnei
  Other enteric bacilli
    Proteus species
      Proteus vulgaris
      Proteus mirabilis
      Proteus morgani
    Pseudomonas aeruginosa
    Alcaligenes faecalis
    Vibrio cholerae
Hemophilus-Bordetella group
  Hemophilus influenzas
    H. ducreyi
    H. hemophilus
    H. aegypticus
    H. parainfluenzae
  Bordetella pertussis
  Pasteurellae
    Pasteurella pestis
    Pasteurella tulareusis
Brucellae
  Brucella melitensis
  Brucella abortus
  Brucella suis
Aerobic Spore-forming Bacilli
  Bacillus anthracis
  Bacillus subtilis
  Bacillus megaterium
  Bacillus cereus
Anaerobic Spore-forming Bacilli
  Clostridium botulinum
  Clostridium tetani
  Clostridium perfringens
  Clostridium novyi
  Clostridium septicum
  Clostridium histolyticum
  Clostridium tertium
  Clostridium bifermentans
  Clostridium sporogenes
Mycobacteria
  Mycobacterium tuberculosis hominis
  Mycobacterium bovis
  Mycobacterium avium
  Mycobacterium leprae
  Mycobacterium paratuberculosis
Actinomycetes (fungus-like bacteria)
  Actinomyces israelii
  Actinomyces bovis
  Actinomyces naeslundii
  Nocardia asteroides
  Nocardia brasiliensis
The Spirochetes
  Treponema pallidum
  Treponema pertenue
  Treponema carateum
  Borrelia recurrentis
  Leptospira icterohemorrhagiae
The Spirochetes con't
  Leptospira canicola
  Spirillum minus
  Streptobacillus moniliformis
Trypanosomas
Mycoplasmas
  Mycoplasma pneumoniae
Other pathogens
  Listeria monocytogenes
  Erysipelothrix rhusiopathiae

*Streptobacillus moniliformis*
*Donvania granulomatis*
*Bartonella bacilliformis*
Rickettsiae (bacteria-like parasites)
  *Rickettsia prowazekii*
  *Rickettsia mooseri*
  *Rickettsia rickettsiae*
  *Rickettsia conori*
  *Rickettsia australis*
  *Rickettsia sibiricus*
  *Rickettsia akari*
  *Rickettsia tsutsugamushi*
  *Rickettsia burnetii*
  *Rickettsia quintana*
Chlamydia (unclassifiable parasites bacterial/vital)
Chlamydia agents (naming uncertain)
Fungi
  *Cryptococcus neoformans*
  *Blastomyces dermatidis*
  *Histoplasma capsulatum*
  *Coccidioides immitis*
  *Paracoccidioides brasiliensis*
  *Candida albicans*
  *Aspergillus fumigatus*
  Mucor corymbifer (*Absidia corymbifera*)
  Phycomycetes
    *Rhizopus oryzae*
    *Rhizopus arrhizus*
    *Rhizopus nigricans*
  *Sporotrichum schenkii*
  *Fonsecaea pedrosoi*
  *Fonsecaea compacta*
  *Fonsecaea dermatidis*
  *Cladosporium carrionii*
  *Phialophora verrucosa*
  *Aspergillus nidulans*
  *Madurella mycetomi*
  *Madurella grisea*
  *Allescheria boydii*
  *Phialosphora jeanselmei*
  *Microsporum gypseum*
  *Trichophyton mentagrophytes*
  *Keratinomyces ajelloi*
  *Microsporum canis*
  *Trichophyton rubrum*
  *Microsporum adouini*
Viruses
Adenoviruses
Herpes Viruses
  Herpes simplex
  Varicella (Chicken pox)
  Herpes Zoster (Shingles)
  Virus B
  Cytomegalovirus
Pox Viruses
  Variola (smallpox)
  Vaccinia
  *Poxvirus bovis*
  Paravaccinia
  *Molluscum contagiosum*
Picornaviruses
  Poliovirus
  Coxsackievirus
  Echoviruses
  Rhinoviruses
Myxoviruses
  Influenza (A, B, and C)
  Parainfluenza (1-4)
  Mumps Virus
  Newcastle Disease Virus
  Measles Virus
  Rinderpest Virus
  Canine Distemper Virus
  Respiratory Syncytial Virus
  Rubella Virus
Arboviruses
  Eastern Equine Encephalitis Virus
  Western Equine Encephalitis Virus
  Sindbis Virus
  Chikungunya Virus
  Semliki Forest Virus
  Mayora Virus
  St. Louis Encephalitis Virus
  California Encephalitis Virus
  Colorado Tick Fever Virus
  Yellow Fever Virus
  Dengue Virus
Reoviruses
  Reovirus Types 1-3
Retroviruses
  Human Immunodeficiency Viruses I and II (HIV)
  Human T-cell Lymphotrophic Virus I & II (HTLV)
Hepatitis
  Hepatitis A Virus
  Hepatitis B Virus
  Hepatitis C Virus
Tumor Viruses
  Rauscher Leukemia Virus
  Gross Virus
  Maloney Leukemia Virus
  Human Papilloma Virus The monoepitopic ligand analytes will generally be from about 100 to 2,000 molecular weight, more usually from 125 to 1,000 molecular weight. The analytes include drugs, metabolites, pesticides, pollutants, and the like. Included among drugs of interest are the alkaloids: morphine alkaloids, which include morphine, codeine, heroin, dextromethorphan, their derivatives and metabolites; cocaine alkaloids, which include cocaine and benzyl ecgonine, their derivatives and metabolites; ergot alkaloids, which include the diethylamide of lysergic acid; steroid alkaloids; iminazoyl alkaloids; quinazoline alkaloids; isoquinoline alkaloids; quinoline alkaloids, which include quinine and quinidine; and diterpene alkaloids, their derivatives and metabolites.

The next group of drugs includes steroids, which includes the estrogens, gestrogens, androgens, adrenocortical steroids, bile acids, cardiotonic glycosides and aglycones, which includes digoxin and digoxigenin, saponins and sapogenins, their derivatives and metabolites. Also included are the steroid mimetic substances, such as diethylstilbestrol.

The next group of drugs is lactams having from 5 to 6 annular members, which include the barbituates, for example, phenobarbital and secobarbital, diphenylhydantonin, primidone, ethosuximide, and their metabolites.

The next group of drugs is aminoalkylbenzenes, with alkyl of from 2 to 3 carbon atoms, which includes the amphetamines; catecholamines, which includes ephedrine, L-dopa, epinephrine; narceine; papaverine; and derivatives and metabolites of the above.

The next group of drugs is benzheterocyclics, which include oxazepam, chlorpromazine, tegretol, their derivatives and metabolites, the heterocyclic rings being azepines, diazepines and phenothiazines.

The next group of drugs is purines, which includes theophylline, caffeine, their metabolites and derivatives.

The next group of drugs includes those derived from marijuana, which includes cannabinol and tetrahydrocannabinol.

The next group of drugs is the hormones such as thyroxine, cortisol, triiodothyronine, testosterone, estradiol, estrone, progesterone, polypeptides such as angiotensin, LHRH, and immunosuppressants such as cyclosporin, FK-506, mycophenolic acid, and so forth.

The next group of drugs includes the vitamins such as A, B, e.g. $B_{12}$, C, D, E and K, folic acid, thiamine.

The next group of drugs is prostaglandins, which differ by the degree and sites of hydroxylation and unsaturation.

The next group of drugs is the tricyclic anti-depressants, which include imipramine, dismethylimipramine, amitriptyline, nortriptyline, protriptyline, trimipramine, chlomipramine, doxepine, and desmethyldoxepin, The next group of drugs are the antineoplastics, which include methotrexate.

The next group of drugs is antibiotics, which include penicillin, chloromycetin, actinomycetin, tetracycline, terramycin, their metabolites and derivatives.

The next group of drugs is the nucleosides and nucleotides, which include ATP, NAD, FMN, adenosine, guanosine, thymidine, and cytidine with their appropriate sugar and phosphate substituents.

The next group of drugs is miscellaneous individual drugs, which include methadone, meprobamate, serotonin, meperidine, lidocaine, procainamide, acetylprocainamide, propranolol, griseofulvin, valproic acid, butyrophenones, antihistamines, chloramphenicol, anticholinergic drugs, such as atropine, their metabolites and derivatives.

Metabolites related to diseased states include spermine, galactose, phenylpyruvic acid, and porphyrin Type 1.

The next group of drugs is aminoglycosides, such as gentamicin, kanamicin, tobramycin, and amikacin.

Among pesticides of interest are polyhalogenated biphenyls, phosphate esters, thiophosphates, carbamates, polyhalogenated sulfenamides, their metabolites and derivatives.

For receptor analytes, the molecular weights will generally range from 10,000 to $2\times10^8$, more usually from 10,000 to $10^6$. For immunoglobulins, IgA, IgG, IgE and IgM, molecular weights will generally vary from about 160,000 to about $10^6$. Enzymes will normally range from about 10,000 to 1,000,000 in molecular weight. Natural receptors vary widely, generally being at least about 25,000 molecular weight and may be $10^6$ or higher molecular weight, including such materials as avidin, DNA, RNA, thyroxine binding globulin, thyroxine binding prealbumin, transcortin, etc.

The term analyte further includes polynucleotide analytes such as those polynucleotides defined below. These include mRNA, rRNA, tRNA, DNA, DNA-RNA duplexes, etc. The term analyte also includes receptors that are polynucleotide binding agents, such as, for example, restriction enzymes, activators, repressors, nucleases, polymerases, histones, repair enzymes, chemotherapeutic agents, and the like.

The analyte may be a molecule found directly in a sample such as a body fluid from a host. The sample, preferably in a suitable medium, can be examined directly or may be pretreated to render the analyte more readily detectable by removing any unwanted materials before the sample is added to the assay medium. Furthermore, the analyte of interest may be determined by detecting an agent probative of the analyte of interest such as a specific binding pair member complementary to the analyte of interest, whose presence will be detected only when the analyte of interest is present in a sample. Thus, the agent probative of the analyte becomes the analyte that is detected in an assay. The body fluid can be, for example, urine, blood, plasma, serum, saliva, semen, stool, sputum, cerebral spinal fluid, tears, mucus, and the like.

Analyte analog or ligand analog ("analog"): a modified analyte or analyte surrogate, modified ligand or ligand surrogate, or organic radical, usually of a molecular weight greater than 100, which can compete with the analogous analyte or ligand for binding to a receptor, the modification providing means to join the analog to another molecule. The term analyte surrogate or ligand surrogate refers to a compound having the capability of specifically binding a receptor complementary to the analyte or ligand. The analog will usually, but not always, differ from the analyte or ligand by more than replacement of a hydrogen with a bond that links the analog to a hub or label. The analog can bind to the receptor in a manner similar to the analyte or ligand. The analog could be, for example, an antibody directed against the idiotype of an antibody to the ligand.

Member of a specific binding pair ("sbp member"): one of two different molecules, having an area on the surface or in a cavity that specifically binds to and is thereby defined as complementary with a particular spatial and polar organization of the other molecule. The members of the specific binding pair can be referred to as ligand and receptor (antiligand) such as when they are members of an immunological pair such as antigen-antibody and hapten-antibody. Other specific binding pairs that are not immunological pairs, are also included in this invention, for example, enzyme-substrate, biotin-avidin, hormones-hormone receptors, nucleic acid duplexes, IgG-protein A, polynucleotide pairs such as DNA-DNA, DNA-RNA.

Ligand: any organic compound for which a receptor naturally exists or can be prepared, and includes antigens and haptens.

Antigen: an immunogen, i.e., any compound capable of binding to an antibody and against which antibodies can be raised.

Hapten: any compound capable of binding specifically to an antibody, but which does not itself act as an immunogen (or antigen) for preparation of the antibodies. Antibodies that recognize a hapten can be prepared against compounds comprised of the hapten linked to an immunogenic (or antigenic) carrier.

Receptor ("antiligand"): any compound or composition capable of recognizing a particular spatial and polar organization of a molecule, e.g., epitopic or determinant site. Illustrative receptors include naturally occurring receptors, e.g., thyroxine binding globulin, antibodies, enzymes, Fab fragments, lectins, nucleic acids, protein A, complement component Clq, and the like.

Antibody: an immunoglobulin that specifically binds to and is thereby defined as complementary with a particular spatial and polar organization of another molecule. The antibody can be monoclonal or polyclonal and can be prepared by techniques that are well known in the art such as immunization of a host and collection of sera (polyclonal) or by preparing continuous hybrid cell lines and collecting the secreted protein (monoclonal), or by cloning and expressing nucleotide sequences or mutagenized versions thereof coding at least for the amino acid sequences required for specific binding of natural antibodies. Antibodies may include a complete immunoglobulin or fragment thereof, which immunoglobulins include the various classes and isotypes, such as IgA, IgD, IgE, IgG1, IgG2a, IgG2b and IgG3, IgM, etc. Fragments thereof may include Fab, Fv and F(ab')$_2$, Fab', and the like. In addition, aggregates, polymers, and conjugates of immunoglobulins or their fragments can be used where appropriate so long as binding affinity for a particular molecule is maintained.

Polynucleotide: a compound or composition that is a polymeric nucleotide having in the natural state about 50 to 500,000 or more nucleotides and having in the isolated state about 15 to 50,000 or more nucleotides, usually about 15 to 20,000 nucleotides, more frequently 15 to 10,000 nucleotides. The polynucleotide includes nucleic acids from any source in purified or unpurified form, naturally occurring or synthetically produced, including DNA (dsDNA and ssDNA) and RNA, usually DNA, and may be tRNA, mRNA, rRNA, mitochondrial DNA and RNA, chloroplast DNA and RNA, DNA-RNA hybrids, or mixtures thereof, genes, chromosomes, plasmids, the genomes of biological material such as microorganisms, e.g., bacteria, yeasts, viruses, viroids, molds, fungi, plants, animals, humans, and fragments thereof, and the like.

Specific binding: the specific recognition of one of two different molecules for the other as compared to substantially less recognition of other molecules. In general, the molecules have areas on their surfaces or in cavities giving rise to specific recognition between the two molecules. Exemplary of specific binding are antibody-antigen interactions, enzyme-substrate interactions, polynucleotide interactions, and so forth.

Non-specific binding: non-covalent binding between molecules that is relatively independent of specific surface structures. Non-specific binding may result from several factors including hydrophobic interactions between molecules.

Linking group: the covalent linkage between molecules. The linking group will vary depending upon the nature of the molecules, i.e., label, sbp member or small molecule, being linked. Functional groups that are normally present or are introduced on such molecules will be employed for linking these materials to one another or to the capillary tube surface.

For the most part, carbonyl functionalities will find use, both oxocarbonyl, e.g., aldehyde; sulfonyl (derived from sulfonic acids); and non-oxocarbonyl (including nitrogen and sulfur analogs) e.g., carboxy, amidine, amidate, thiocarboxy and thionocarboxy. As used herein, the term "non-oxocarbonyl" shall include the carbonyl group of carboxylic acids, —COOH; the nitrogen containing imino-carbonyl group of amidic acids, —C(NH)OH; and the sulfur containing thionocarbonyl group of thio acids, —C(S)OH. Alternative functionalities of oxo include active halogen, diazo, mercapto, olefin, particularly activated olefin, amino, phosphoro and the like. A description of linking groups may be found in Rubenstein, et al., U.S. Pat. No. 3,817,837, which disclosure is incorporated herein by reference.

The linking groups may vary from a bond to a chain of from 1 to 100 atoms, usually from about 1 to 70 atoms, preferably 1 to 50 atoms and more preferably 1 to 20 atoms, each independently selected from the group normally consisting of carbon, oxygen, nitrogen, sulfur and phosphorous. The number of heteroatoms in the linking groups will normally range from about 0 to 20, usually from about 1 to 15, more preferably 2 to 6. The atoms in the chain may be substituted with atoms other than hydrogen in a manner similar to that described for the substituent having from 1 to 50 atoms. As a general rule, the length of a particular linking group can be selected arbitrarily to provide for convenience of synthesis and the incorporation of any desired group. The linking groups may be aliphatic or aromatic, although with diazo groups, aromatic groups will usually be involved.

Common functionalities in forming a covalent bond between the linking group and the molecule to be conjugated are carboxamides, thiocarboxamides, carbamates, thiocarbamates, carboxylic acid esters, thioesters, sulfonic acid esters, phosphoric acid esters, ureas, thioureas, carbamates, phosphoramides, sulfonamides, ethers, sulfides, thioethers, olefins, acetylenes, amines, amidines, amides, thioamides, ketones, and the like. The chain of the linking group can contain more than one of the above functionalities, usually one to two of the above functionalities.

The atoms in the chain may be substituted with atoms other than hydrogen. Generally, the predominant atom as a substituent is hydrogen (H) but may also be halogen (chlorine, bromine and fluorine), oxygen (O), nitrogen (N), sulfur (S), phosphorus (P), wherein the O, N, S, or P, if present, are bound to carbon or one or more of each other or to hydrogen to form various functional groups, such as, for example, carboxylic acids, alcohols, thiols, carboxamides, carbamates, carboxylic acid esters, thioesters, sulfonic acids, sulfonic acid esters, phosphoric acids, phosphoric acid esters, ureas, thioureas, carbamates, phosphoramides, sulfonamides, ethers, sulfides, thioethers, olefins, acetylenes, amines, amidines, amides, thioamides, ketones, aldehydes, nitriles, and the like. Illustrative of such organic radicals or groups, by way of illustration and not limitation, are alkyl, alkylidine, aryl, aralkyl, and alkyl, aryl, and aralkyl substituted with one or more of the aforementioned functionalities.

When heteroatoms are present, oxygen will normally be present as oxo or oxy, bonded to carbon, sulfur, nitrogen or phosphorous; nitrogen will normally be present as nitro, nitroso or amino, normally bonded to carbon, oxygen, sulfur or phosphorous; sulfur would be analogous to oxygen; while phosphorous will be bonded to carbon, sulfur, oxygen or nitrogen, usually as phosphonate and phosphate mono- or diester.

Label: any molecule that produces or can be induced to produce a signal. The label may be conjugated to an analyte or an antibody, or to another molecule such as a receptor or a molecule that can bind to a receptor such as a ligand, particularly a hapten. In the subject invention, the label is a member of the signal producing system, as defined below, that includes a signal producing means.

Small molecule: a small molecule or a residue of a small molecule, having a molecular weight of from 100 to 2000, preferably 150 to 1000, for which a receptor exists or can be prepared. Examples of such small molecules include derivatives of biotin, lysergic acid, fluorescein or a fluorescein derivative, and vitamin $B_{12}$, with the corresponding receptors being avidin or streptavidin, anti-lysergic acid, anti-fluorescein and intrinsic factor, respectively.

Signal producing system ("sps"): the function of the signal producing system is to produce a product that provides a detectable signal related to the amount of bound and/or unbound label. There are numerous methods by which the label can produce a detectible signal, for example by electromagnetic radiation, heat, chemical reagents, and the like.

The signal producing system may have one or more components, at least one component being the label conjugated to an sbp member.

The label can directly produce a signal, i.e., additional reagents are not required to produce a signal. For example, numerous organic molecules are able to absorb ultraviolet and visible light, where the light absorption transfers energy to these molecules and elevates them to an excited energy state. This absorbed energy is then dissipated by emission of light at a second wavelength. For example, fluorescent molecules are able to absorb light at one wavelength and emit light at a second wavelength.

Suitable fluorescent molecules include fluorescein, isothiocyanate, rhodamine, phycoerythrin, phycocyanin, allophycocyanin, o-phthaldehyde, and fluorescamine. A large number of illustrative fluorescers are indicated in Litman, et al., U.S. Pat. No. 4,275,149, columns 30 and 31, which disclosure is incorporated herein by reference. Other examples of labels that can directly produce a signal are radioactive isotopes, such as $^{125}$I, $^{131}$I, $^{14}$C, $^{3}$H, $^{57}$Co and $^{75}$Se, and the like; and dyes, such as are well known in the art.

Alternately, the label may also require other reagents in order to produce a signal. Therefore, the signal producing system includes all of the reagents required to produce a measurable signal including the first sbp member when conjugated to a label and the components of the developer. When the first sbp member is not conjugated to a label, the label is normally bound to an sbp member complementary to the first sbp member and is usually included as part of the developer. Other components of the developer include substrates, coenzymes, enhancers, second enzymes, activators, cofactors, inhibitors, scavengers, metal ions, specific binding substance required for binding of signal generating substances, and the like. Some of the chemical reagents such as coenzymes, substances that react with enzymic products, other enzymes and catalysts, and the like can be bound to other molecules or to a support.

The signal producing system provides a signal detectable by external means, normally by measurement of electromagnetic radiation, desirably by visual examination.

For example, the signal producing system can include a chromophoric substrate and enzyme, where the chromophoric substrate is enzymatically converted to a dye that absorbs light in the ultraviolet or visible region, phosphors or fluorescers.

The signal-producing system can include at least one catalyst, usually at least one enzyme, and at least one substrate and may include two or more catalysts and a plurality of substrates, and may include a combination of enzymes, where the substrate of one enzyme is the product of the other enzyme. The operation of the signal producing system is to produce a product that provides a detectable signal related to the amount of catalyst bound to the support, as a result of sbp member complex formation of the labeled sbp member.

The signal producing system provides for the production of a compound, which is normally the signal generating compound, but in some instances may react with another compound bound to the surface with the production, enhancement or destruction of the signal generating compound. While both enzymatic and non-enzymatic catalysts may be employed, usually there will be at least one enzyme catalyst employed in the signal producing system. In the event of there being only one catalyst, this catalyst will usually be conjugated to an sbp member through sbp member complex formation. In addition to the catalyst, there must be a substrate that undergoes a transformation, which results in a change in a detectable signal at the measurement surface. For the most part, the product resulting from the transformation catalyzed by the labeled sbp member will be the signal generating compound.

Two catalysts may be employed, either a combination of an enzyme and a non-enzyme catalyst or two enzymes, where the two catalysts are related in that the product of one is the substrate of the other. In this system, there need be only one substrate that can undergo successive changes catalyzed by the catalysts, which results in the compound involved with production of a detectable signal. For the most part, however, there will normally be a substrate for the first enzyme in the series and a second compound, which serves as a precursor to the compound involved in the production of the signal, normally providing the compound that produces the signal. Thus, the product of the first enzyme may react with the precursor to the signal producing compound to provide the signal generating compound.

For the most part, the involved reactions will be hydrolysis or redox reactions. In the case of hydrolysis, a derivatized dye precursor that has an enzymatically labile bond and an enzyme that catalyzes its conversion to an insoluble dye product is illustrative of this type of system. In redox reactions, a first enzyme would produce an essential oxidizing substrate for the second enzyme, where the second enzyme catalyzes the reaction between the oxidizing substrate and a dye precursor.

Where two enzymes are used, the first enzymatic reaction may involve hydrolytic cleavage or a redox reaction of the substrate to provide a product that is the substrate of another enzyme. The first situation may be illustrated by glucose-6-phosphate being catalytically hydrolyzed by alkaline phosphatase to glucose, where glucose is a substrate for glucose oxidase. The second situation may be illustrated by glucose being oxidized by glucose oxidase to provide hydrogen peroxide that would enzymatically react with a leuco dye to produce a signal generator.

Coupled catalysts can also involve an enzyme with a non-enzymatic catalyst. The enzyme can produce a reactant that undergoes a reaction catalyzed by the non-enzymatic catalyst or the non-enzymatic catalyst may produce a substrate (includes coenzymes) for the enzyme. A wide variety of non-enzymatic catalysts that may be employed are found in Ullman, U.S. Pat. No. 4,160,645, the appropriate portions of which are incorporated herein by reference.

Various combinations of enzymes may be employed to provide a signal generating compound. Particularly, combinations of hydrolases may be employed to produce an insoluble signal generator. Alternatively, combinations of hydrolases and oxidoreductases can provide the signal generating compound.

For combinations of enzymes one enzyme can be non-diffusively bound to the capillary tube, while the other enzyme is conjugated to a sbp member. Additionally, one or more other members of the signal producing system can be bound to the tube depending on the particular signal producing system chosen or the particular protocol followed.

Because of the nature of the signal, in order to have a detectable signal, it is desirable to provide means for amplifying the signal produced by the presence of the label. Therefore, it will usually be preferable for the label to be a catalyst or luminescent compound, most preferably a catalyst. Preferable catalysts are enzymes and coenzymes, which can produce a multiplicity of signal generating molecules from a single label.

An enzyme or coenzyme is employed that provides the desired amplification by producing a product, which absorbs light, e.g., a dye, or emits light upon irradiation, e.g., a fluorescer. Alternatively, the catalytic reaction can lead to direct light emission, e.g., chemiluminescence. A large number of enzymes and coenzymes for providing such products are indicated in Litman, et al., U.S. Pat. No. 4,275,149 bridging columns 19 to 23, and Boguslaski, et al., U.S. Pat. No. 4,318,980, columns 10 to 14, which disclosures are incorporated herein by reference.

Of particular interest is the use of a combination of enzymes, where the enzymes are related by the product of one enzyme being the substrate of the other enzyme. In this manner, stable precursors to labile substrates can be provided and the substrate for a second enzyme can be stored in combination with a first enzyme without a reaction being prematurely initiated.

A number of enzyme combinations are set forth in Litman, et al., U.S. Pat. No. 4,275,149, bridging columns 23 to 28, which combinations can find use in the subject invention. This disclosure is incorporated herein by reference.

Of particular interest are enzymes that involve the production of hydrogen peroxide and the use of the hydrogen peroxide to oxidize a dye precursor to a dye. Particular combinations include saccharide oxidases, e.g., glucose and galactose oxidase, or heterocyclic oxidases, such as uricase and xanthine oxidase, coupled with an enzyme that employs the hydrogen peroxide to oxidize a dye precursor, i.e., a peroxidase such as horseradish peroxidase, lactoperoxidase, and microperoxidase. Additional enzyme combinations may be found in the subject matter incorporated by reference.

When a single enzyme is used as a label, other enzymes may find use such as hydrolases, transferases, and oxidoreductases preferably hydrolases such as alkaline phosphatase and β-galactosidase. Alternatively, luciferases may be used such as firefly luciferase and bacterial luciferase.

Illustrative coenzymes that find use include NAD[H]; NADP[H], pyridoxal phosphate; FAD[H]; FMN[H], etc., usually coenzymes involving cycling reactions, see particularly U.S. Pat. No. 4,318,980.

The product of the enzyme reaction will usually be a dye or fluorescer. A large number of illustrative fluorescers are indicated in Litman, et al., U.S. Pat. No. 4,275,149, columns 30 and 31, which disclosure is incorporated herein by reference.

Chemiluminescent compounds are also suitable as labels such as, by means of illustration and not limitation, luminol, isoluminol, aromatic acridinium esters, imidazole, acridinium salt, oxalate ester, and the like. Numerous chemiluminescers are set forth in Litman, et al., U.S. Pat. No. 4,275,149, column 31, which disclosure is incorporated herein by reference.

Ancillary materials: Various ancillary materials will frequently be employed in the assay in accordance with the present invention. For example, buffers will normally be present in the assay medium, as well as stabilizers for the assay medium and the assay components. Frequently, in addition to these additives, proteins may be included, such as albumins; organic solvents such as formamide; quaternary ammonium salts; polyanions such as dextran sulfate; surfactants, particularly non-ionic surfactants; binding enhancers, e.g., polyalkylene glycols; or the like. As mentioned above, the present invention concerns a method of determining an analyte where a medium suspected of containing an analyte is drawn into a capillary tube by capillary action, such that if the analyte is present, it becomes immobilized in the tube. This medium is expelled from the tube and, optionally, one or more additional reagents are similarly drawn up and expelled. When the last fluid is expelled from the tube, a pendulous drop is caused to form at the opening of the capillary tube. This pendulous drop of fluid is then examined to detect the presence or intensity of signal, which is related to the presence or amount of analyte in the medium. As used herein the term "pendulous drop" is intended to mean a portion of the medium hanging downward, i.e., suspended from the bottom opening to form an attached droplet.

Figure 1:
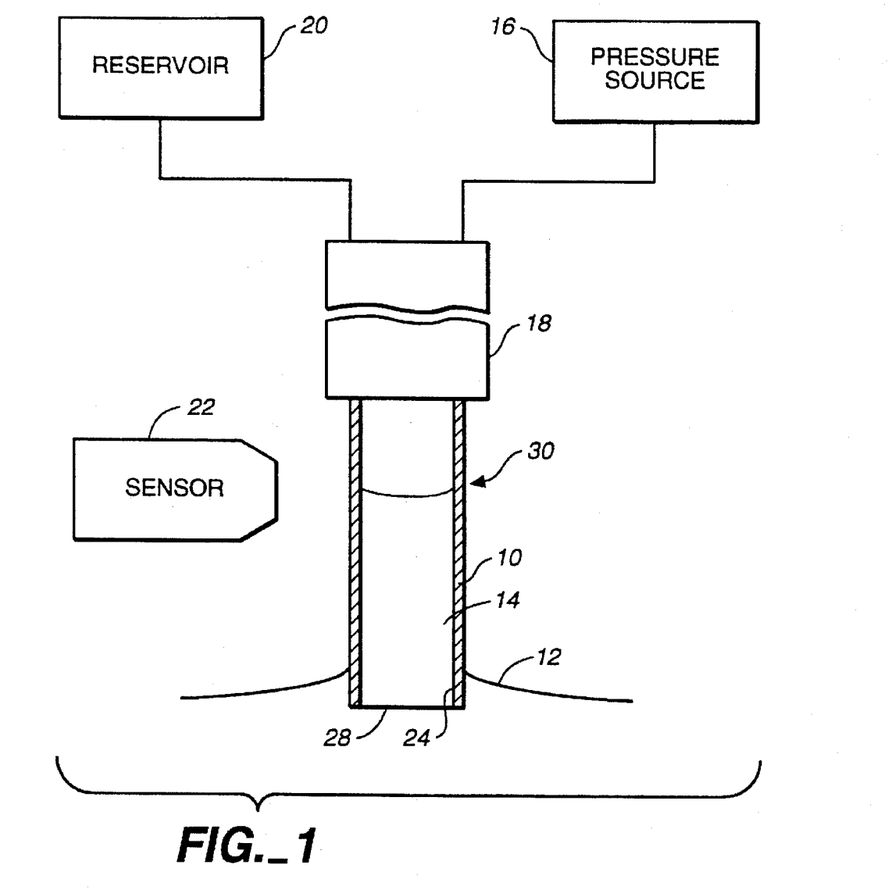
FIG. 1 is a longitudinal cross-section of the capillary tube used in the method of this invention.
Figure 2:
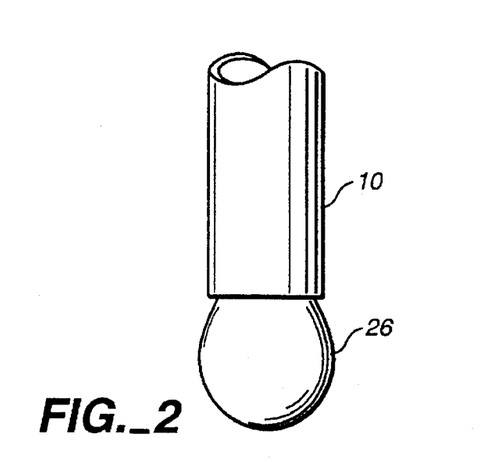
FIG. 2 is a schematic of the pendulous drop formed in the method of this invention.

The method of this invention is illustrated, by way of example and not limitation, with reference to the drawings of FIG. 1 and 2. In FIG. 1, capillary tube 10 is dipped into liquid medium 12, where the medium is suspected of containing the analyte and/or contains assay reagent(s).

A fixed volume 14 is drawn into the tube by capillary action. The surface tension of the liquid medium allows the medium to remain in the tube for a sufficient period of time so as to permit the analyte or reagents to react with any reagents already bound to the inner surface of the capillary tube.

The volume of the liquid drawn into the capillary tube may be controlled solely by the diameter of the capillary, and will be within the range of 6–14 μL. However, since the surface tension of the liquid medium is unknown in most situations and the diameter of the capillary may have some tolerance, the volume 14 of medium drawn into the tube may not be controllable by capillarity alone.

One means of controlling volume 14 to provide an accurate and reproducible assay involves drawing the medium a fixed distance into the capillary by negative pressure provided by an external pressure source 16, connected to the capillary 10 by means of connector 18, which also serves as the connector to the wash solution reservoir 20. The distance the medium is drawn in to the capillary is determined by a sensor 22, and is within the range of 15–200 mm. In this manner, the volume of medium containing the analyte or assay reagent in the tube can be accurately controlled. Other means will be suggested to those skilled in the art.

The medium suspected of containing the analyte is incubated in the capillary so that analyte, if present, is captured on the inside surface 24 of the capillary 10, such as by binding to a specific binding pair member. The medium is expelled and each assay reagent or combination thereof, in an appropriate medium, is drawn into the capillary, allowed to incubate and then expelled.

After completion of each incubation, the medium is preferably expelled by one or more washings with a suitable wash solution pushed through the capillary. This allows for the removal of any unbound reagents. The method of this invention preferably has from 2–4 washes, the actual number depending on the number of different incubations or the number of steps involved in the assay. Each wash is preferably 3–8 fold, more preferably 4–7 fold and most preferably, 6 fold. Each fold wash uses a volume approximately equal to the reaction volume of the capillary, such that, for example, for a 10 μL reaction volume, a 6 fold wash would involve washing the capillary tube with 60 μL of wash solution.

When the last assay reagent-containing medium is drawn into the capillary and has been allowed to incubate, the medium in the capillary is sufficiently expelled from the capillary to form a pendulous drop 26, as illustrated in FIG. 2. This expelling of the final medium is accomplished by positive pressure provided by the external pressure source 16. If it should prove advantageous for a particular assay that there be a kinetic measurement of signal intensity, the pendulous drop could be drawn back into the capillary after the first measurement to let interaction of the signal producing members' interaction continue. The drop can then be reformed for a second measurement.

More specifically, the method of this invention involves a method of determining an analyte comprising the steps of: drawing a first medium suspected of containing an analyte into a capillary tube to capture therein the analyte, if present; expelling the first medium from the tube; drawing a second medium containing a labeled sbp member into the tube if the first medium does not contain a labeled sbp member, wherein the labeled sbp member is capable of binding the analyte or a second sbp member capable of binding the analyte; expelling the second medium from the tube; drawing a third medium containing reagents for producing a signal from the label if the label is not capable of directly producing a signal; expelling the third medium from the tube; and examining a drop of the first medium or the second or third medium, if a second or third medium is used, for the presence or intensity of the signal, the presence or intensity thereof being related to the presence or amount of analyte in the first medium.

The analyte and sbp members are each independently selected from the group consisting of ligands, receptors, and polynucleotides.

The analyte can be captured in the capillary in numerous ways as described herein. For example, the inner surface of the capillary tube can be coated with an sbp member capable of specifically binding the analyte. Alternatively, the tube can be coated with a receptor for a small molecule that is bound to an sbp member capable of specifically binding the analyte, for example an avidin coated tube and a biotinylated sbp member. Some analytes, for example, microorganisms such as bacteria, e.g. chlamydia, are easily adsorbed onto support surfaces, such as plastic, without the need for a specific binding pair member.

As stated above, the labeled sbp member can bind the analyte directly or indirectly by binding a second sbp member capable of binding the analyte. In one embodiment, the second sbp member can be bound to a small molecule and the label bound to a receptor for the small molecule, for example, a fluorescein-bound sbp member capable of binding the analyte and the labeled sbp member can be a labeled-anti-fluorescein antibody.

The first medium can also contain a labeled sbp member that is an analog of the analyte. In that instance, a separate medium containing a labeled sbp member, described above as the "second" medium, would not be required.

The label can be capable of directly producing a signal, such as a fluorophor that fluoresces when contacted by light. In another embodiment, the label is, for example, an enzyme that requires a substrate to exhibit enzymatic activity. In this instance, an additional third medium containing the remaining members of the signal producing system, such as an appropriate substrate, would be required. This is described above as the "third" medium. For the fluorophor label, this additional medium would not be necessary.

The method of the invention may be adapted to most heterogeneous assays involving sbp members such as ligand-receptor, e.g., antigen-antibody reactions, polynucleotide binding assays, and so forth. Exemplary heterogeneous assays are found in Zuk, et al., U.S. Pat. No. 4,256,834 and Ullman, et al., U.S. Pat. No. 4,261,968. The assays may have a competitive or sandwich format and conditions are chosen such that an sbp member complex is formed in relation to the presence of the analyte. The analyte and sbp members are each independently selected from the group consisting of ligands, receptors, and polynucleotides.

In a competitive format a label is covalently bound to an sbp member that is analogous to, usually a derivative of, the analyte. The immunological reaction usually involves this labeled sbp member, a second sbp member that is complementary to both the analyte and the labeled sbp member, bound to the inner surface of the capillary tube, and the medium suspected of containing the analyte of interest. In a sandwich format, the immunological reaction usually involves an sbp member, e.g., an antibody, that is complementary to the analyte and bound to the inner surface of the capillary tube, a second sbp member, e.g., antibody, that is also complementary to the analyte and bound to a label, and the medium suspected of containing the analyte of interest.

In one embodiment of the method of this invention, a first medium suspected of containing an analyte is drawn into a capillary tube. The capillary tube has bound thereto a first specific binding pair ("sbp") member capable of binding the analyte. The first medium and first sbp member are incubated so that a first complex involving the analyte and the first sbp member is formed in relation to the presence of analyte in the first medium. The first medium is then expelled from the tube and a second medium containing a labeled second sbp member is drawn into the tube. The labeled second sbp member is capable of binding the analyte or a third sbp member capable of binding the analyte. The labeled second sbp member and the first complex, if present, are incubated to form a labeled complex. If the label is capable of directly producing a signal, the second medium is expelled from the tube to form a pendulous drop, which is examined for the presence or intensity of the signal. However, if the label is not capable of directly producing a signal, a third medium is drawn into the tube, which contains reagents for producing a signal from the label. The third medium is then expelled from the tube to form a pendulous drop, which is examined for the presence or intensity of the signal. The presence or intensity of the signal is indicative of the presence or amount of analyte in the first medium.

As stated above, conditions are chosen such that an sbp member complex is formed in relation to the presence of the analyte, in this instance, the first sbp member is capable of binding to the analyte to form a complex related to the presence of the analyte.

In another embodiment of the method of this invention, a first medium suspected of containing an analyte is drawn into a capillary tube. The first medium also contains a labeled analog of the analyte and the capillary tube has bound thereto a specific binding pair ("sbp") member capable of binding the analyte and the labeled analog. If the label is capable of directly producing a signal, the first medium is expelled from the tube to form a pendulous drop, which is examined for the presence or intensity of the signal. However, if the label is not capable of directly producing a signal, the first medium is expelled from the tube and a second medium is drawn into the tube, which contains reagents for producing a signal from the label. The second medium is then expelled from the tube to form a pendulous drop, which is examined for the presence or intensity of signal. The presence or intensity of the signal is indicative of the presence or amount of analyte in the first medium.

Conditions are chosen such that an sbp member complex is formed in relation to the presence of the analyte. For example, the sbp member is capable of binding to the analyte or to the labeled analog of the analyte to form a complex related to the presence of the analyte.

The wash solutions and solutions containing the assay reagents in the above-described assays, will normally consist of aqueous buffered medium at a moderate pH, generally that which provides optimum assay sensitivity. The aqueous medium may be solely water or may include a polar solvent.

Suitable polar cosolvents are oxygenated organic cosolvents of from 1–6, more usually from 1–4 carbon atoms, including alcohols, ethers, esters, haloalkanes, sulfoxides, amides, and the like. These polar solvents will be present in less than about 40 weight percent, more usually in less than about 20 weight percent.

The pH for the medium will usually be in the range of about 4 to 11, more usually in the range of about 5 to 10, and preferably in the range of about 5.4 to 9.5. The pH is chosen so as to maintain a significant level of binding between sbp members while optimizing signal producing proficiency. In addition the pH is chosen to provide adequate stability of each of the reagents and the analyte. Various buffers may be used to achieve the desired pH and maintain the pH during the determination. Illustrative buffers include borate, phosphate, carbonate, Tris, barbital and the like. The particular buffer employed is not critical to this invention, but in an individual assay one or another buffer may be preferred.

Moderate temperatures are normally employed for carrying out the assay and usually constant temperature, preferably, room temperature, during the period of the measurement of the signal. Incubation temperatures will normally range from about 5° to 99° C., usually from about 15° to 70° C., more usually 20° to 45° C. Temperatures during measurements will generally range from about 10° to 70° C., more usually from about 20° to 45° C., more usually 20° to 25° C.

Incubation times generally range from about 30 seconds to 6 hours, more usually from about 2 minutes to 1 hour.

The concentration of analyte that may be assayed will generally vary from about $10^{-5}$ to $10^{-20}$M, more usually from about $10^{-6}$ to $10^{-14}$M.

While the concentrations of the various reagents in the assay medium will generally be determined by the concentration range of the analyte, the final concentration of each of the reagents will normally be determined empirically to optimize the sensitivity of the assay over the range of interest. That is, a variation in concentration of the analyte that is of significance should provide an accurately measurable signal difference. The total binding sites of the members of the specific binding pair that are complementary to the analyte will not be less than about 0.1 times the minimum concentration of interest based on binding sites of the analyte and not more than about 10,000 times the maximum concentration of interest based on analyte binding sites, usually about 0.1 to 1000 times, usually about 0.3 to 10 times the maximum concentration of interest. For a ligand analyte, where a labeled ligand is employed, the concentration range of the labeled ligand based on equivalents will generally not be less than about $10^{-6}$, more usually not less than $10^{-2}$, times the minimum concentration of interest and not greater than 100, usually not greater than 10, times the maximum concentration of interest.

Other considerations, such as whether the assay is qualitative, semiquantitative or quantitative, and the particular detection technique used, also affect selection of the various reagent concentrations.

As indicated above, the method of this invention utilizes a capillary tube. The capillary tube may be made of any suitable material, preferably glass, plastic or a synthetic resin, for example, polyethylene, polycarbonate, polypropylene, polystyrene, acrylic resin or the like.

The capillary tube has a bore diameter of preferably 0.2–2.0 mm, more preferably 0.3–1.0 mm, and most preferably 0.4 mm. The full length of the capillary tube is not used in the assay; rather, the "active" length is the area interacting with the various media drawn into the capillary. This is shown in FIG. 1 as the area and/or volume between the bottom opening 28 of the capillary 10 where the media are drawn in the capillary, and the location 30 observed by sensor 22, which is the farthest most point from the bottom opening 28 where the media are drawn to. Accordingly, the active length of the tube is preferably 15–200 mm, more preferably 40–150 mm, and most preferably about 50 mm. A suitable volumetric capacity of a capillary tube useful in the method of this invention is preferably 6–14 µL, more preferably 8–12 µL, and most preferably about 10 µL. The parameters are selected to provide an optimum surface to volume ratio of 8–12 mm$_2$/µL, more preferably 9–11 mm$_2$/µL, and most preferably about 10 mm$_2$/µL.

As noted above, the analyte can be captured in the capillary tube by numerous ways that are well known to one skilled in the art. In one embodiment of the invention, the analyte reacts with the bare capillary tube, i.e., a capillary tube whose inner surface is untreated or uncoated with either proteins or an sbp member capable of directly or indirectly binding the analyte. By means of illustration and not limitation, antigens such as gram-negative bacteria, can be adsorbed or coated directly onto a surface, such as is described in Milburn, et al., U.S. Pat. No. 4,959,303 and Armstrong, et al., U.S. Pat. No. 4,497,899 at columns 2 to 3; which disclosures are incorporated herein by reference.

In another embodiment of the invention, the analyte is captured by an sbp member capable of specifically binding to the analyte, which is directly coated or bound onto the inner surface of the capillary tube. By means of illustration and not limitation, an antigenic analyte can be captured by antibodies bound inside the tube, and an antibody analyte can be captured by an anti-human antibody or an antigen coated inside the tube. In another embodiment of the invention, the sbp member is indirectly bound to the inside of the capillary tube, where the sbp member is bound to a small molecule and a receptor for the small molecule is coated onto the tubes. For example, avidin, coated onto the tube, can bind a biotinylated antibody, which in turn can bind an antigenic analyte.

Binding of sbp members to the inside of the capillary tube may be accomplished by well-known techniques, commonly available in the literature. See, for example, "Immobilized Enzymes," Ichiro Chibata, Halsted Press, New York (1978) and Cuatrecasas, *J. Biol. Chem.* 245 (12):3059 (1970). The capillary surface is capable of binding an sbp member through specific, non-specific, covalent or non-covalent interactions.

A wide variety of functional groups can be incorporated to facilitate covalent binding of the sbp member to the capillary surface. Such functional groups include carboxylic acids, aldehydes, amino groups, cyano groups, ethylene groups, hydroxyl groups, mercapto groups, and the like. The manner of linking a wide variety of compounds to surfaces is well known and is amply illustrated in the literature. See for example Cuatrecasas, supra. The length of a linking group to the sbp member may vary widely, depending upon the nature of the compound being linked, the effect of the distance between the compound being linked and the surface on the specific binding properties and the like.

A compound such as avidin or streptavidin can also be bound to the capillary and used to capture a biotinylated sbp member. Avidin coating and biotinylation can be done by a variety of methods well described in the literature.

When the last assay reagent-containing medium is drawn into the capillary and subsequently expelled, the medium is preferably expelled to form a pendulous drop 26, as illustrated in FIG. 2. To realize a precision assay the drop size must be effectively reproducible from capillary to capillary. The following are several ways, by way of illustration and not limitation, that an effectively reproducible drop is formed according to this invention.

The drop size is generally limited by the surface tension of the fluid. For a capillary volume of about 6–14 µL, the drop will be about 2.25–2.98 mm in diameter.

Figure 3:
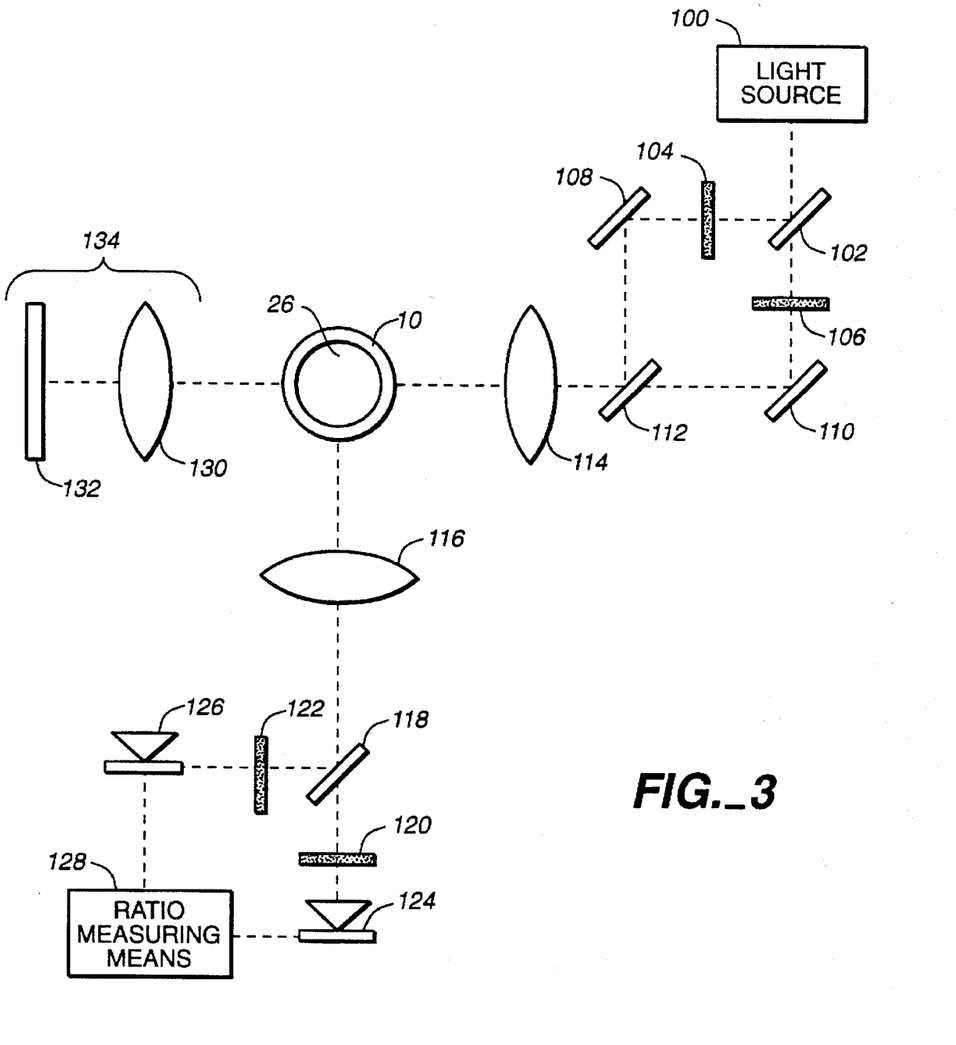
FIG. 3 is a schematic view of a fluorometric detection set-up for use in the method of this invention.

In one embodiment of the invention, the drop size is controlled by controlling the pressure behind the fluid in the capillary. This can be accomplished by a volume of air or liquid behind the measured fluid. In another embodiment the drop size can be controlled by a projected image size sensor such as is well known to those skilled in the art. This is accomplished by projecting an image of the drop diameter onto a linear diode array system 134, as shown in FIG. 3.

The signal produced by the label of this invention can be measured visually, photographically, actinometrically, spectrophotometrically or by any other convenient means to determine the amount thereof, which is related to the amount of analyte in the medium. For example, the signal produced by a fluorophor label is measured by a conventional fluorescent spectrometer; the signal produced by a radioactive isotope label is measured by a gamma counter or a scintillation counter. Other examples of labels and methods of measurement are well known to those skilled in the art.

The following example is offered byway of illustration and not by way of limitation.

In the method of the present invention the solid phase is capillary 10, which is coated on the inside with an antibody specific for the analyte of interest. Capillary 10 has an inside diameter of 0.4 mm and an active length of 50 mm. The active volume of the capillary is about 6.3 µL.

The surface to volume ratio is 10 $mm^2/\mu L$.

To perform an ELISA assay by the sandwich technique capillary 10 is dipped into first medium 12 suspected of containing the analyte and a fixed volume is drawn a fixed distance by negative pressure. The distance the sample is drawn is determined by a sensor 22.

The incubation time for the first medium is about 5 minutes. After completion of the incubation, the first medium is expelled by a wash solution from reservoir 20 pushed through the capillary. About 40 µL of wash solution produces a 6-fold wash.

Following the wash, a second medium, containing an enzyme-labeled antibody, is drawn into the capillary and allowed to incubate for about one minute. When the incubation is complete, the second medium is expelled with wash solution.

A third medium, containing a fluorogenic enzyme substrate (FES) is drawn into the capillary and incubated.

The FES also contains an internal fluorescence standard (IFS) so that the FES fluoresces, whether or not an enzyme-substrate reaction has occurred. When the substrate and enzyme react, the resulting enzyme liberated fluorochrome (EFC) has an excitation wavelength that is sufficiently far removed from the emission wavelength of the IFS that the emission intensity of the IFS is not affected by internal energy transfer from the EFC.

After incubation for about 15 seconds to 4 minutes, a drop is produced by positive pressure from 16 through the connector 18 and the intensity of fluorescence produced by the EFC is compared to that of the IFS. The measurement is either after a fixed time or as a kinetic measurement.

To measure the fluorescence of the EFC and the IFC, the liquid in the capillary is sufficiently expelled from the capillary to form a pendulous drop 26. The drop diameter is controlled approximately by linear diode array system 134, which is made up of lens 130 and linear diode array 132.

The pendulous drop 26 is illuminated by two excitation wavelengths. The two wavelengths are formed from a single light source 100 by a dichroic beamsplitter 102. The light source can be for example, a mercury lamp, tungsten-halogen lamp, flash lamp, laser or the like. Filter 104 isolates the excitation wavelength for the EFC, and filter 106 isolates the excitation wavelength for the IFS. The system is folded by mirrors 108 and 110, and the two excitation wavelengths are combined by dichroic 112. The two wavelengths are focused onto drop 26 by lens 114.

The fluorescence from the drop is collected by lens 116. The two fluorescent emissions are separated by dichroic beamsplitter 118. The EFC emission passes through filter 120, the IFS emission through filter 122. The emission from the EFC is measured by photodetector 124, and that from the IFS by photodetector 126. The ratio of intensities is determined by any of several well known ratio measuring means 128. For example, the intensities detected by photodetectors 124 and 126 can be transduced into voltages, the voltages compared and then read out on means 128 as a printed value or alphanumeric display.

Alternately, means 128 can be a radio amplifier where the output signal is proportional to the ratio of the input signals from the EFC and IFS emission. In this case, means 128 also includes a display connected to the output of the amplifier.

Although the foregoing invention has been described in some detail by way of illustration and example for the purposes of clarity and understanding, it will be obvious that certain changes or modifications may be practiced within the scope of the appended claims.

What is claimed is:

1. A method of determining an analyte comprising the steps of:
   (a) drawing a first medium suspected of containing an analyte into a capillary tube to capture therein said analyte, if present;
   (b) expelling said first medium from said tube;
   (c) drawing a second medium containing a labeled first specific binding pair member into said tube if said first medium does not contain a labeled first specific binding pair member, wherein said labeled first specific binding pair member specifically binds said analyte or specifically binds a second specific binding pair member that specifically binds said analyte, where said second specific binding pair member is optionally present in said first or second medium;
   (d) expelling said second medium from said tube;
   (e) drawing a third medium containing reagents for producing a signal from said label if said label is not capable of directly producing a signal;
   (f) expelling said third medium from said tube, wherein said first, said second or said third medium, if said second or said third medium is used, is expelled to form a pendulous drop;
   (g) said pendulous drop remains outside of, but attached to said tube during examining, then examining said pendulous drop for the presence or intensity of said signal, the presence or intensity thereof being related to the presence or amount of analyte in said first medium.

2. The method of claim 1 wherein said analyte and specific binding pair members are each independently selected from the group consisting of ligands, receptors, and polynucleotides.

3. The method of claim 2 wherein said analyte is coated directly on the surface of said capillary tube in step (a).

4. The method of claim 1 wherein the inner surface of said capillary tube is coated with a specific binding pair member that specifically binds said analyte.

5. The method of claim 1 wherein the inner surface of said capillary tube is coated with a receptor for a small molecule, where said small molecule is bound to a specific binding pair member that specifically binds said analyte.

6. The method of claim 5 wherein said small molecule has a molecular weight of about 150–1000.

7. The method of claim 6 wherein said small molecule is biotin and said receptor is selected from the group consisting of avidin and streptavidin.

8. The method of claim 2 wherein said labeled first specific binding pair member specifically binds said analyte.

9. The method of claim 8 wherein said labeled first specific binding pair member is an antibody.

10. The method of claim 8 wherein said first medium contains said labeled specific binding pair member and said second medium is not used.

11. The method of claim 2 wherein said labeled first specific binding pair member specifically binds said second specific binding pair member.

12. The method of claim 11 wherein said second specific binding pair member is bound to a small molecule and said labeled first specific binding pair member is a labeled receptor for said small molecule.

13. The method of claim 12 wherein said small molecule is selected from the group consisting of fluorescein and fluorescein derivatives, said labeled receptor is a labeled anti-fluorescein antibody.

14. The method of claim 2 wherein said labeled first specific binding pair member is an analyte analog.

15. The method of claim 1 wherein said first medium contains said labeled first specific binding pair member and said second medium is not used.

16. The method of claim 1 wherein said label is able to directly produce a signal and said third medium is not used.

17. The method of claim 16 wherein said label is selected from the group consisting of fluorophors and radiolabels.

18. The method of claim 1 wherein said label is not capable of directly producing a signal.

19. The method of claim 18 wherein said label is selected from the group consisting of enzymes and chemiluminescers.

20. The method of claim 18 wherein said second medium is expelled by one or more wash solutions pushed through said capillary.

21. The method of claim 18 wherein said label is an enzyme and said third medium contains a substrate for said enzyme.

22. The method of claim 21 wherein said label is an enzyme selected from the group consisting of horseradish peroxidase, β-galactosidase, uricase and alkaline phosphatase.

23. The method of claim 1 wherein said first medium is expelled by one or more wash solutions pushed through said capillary.

24. A method of determining an analyte comprising the steps of:
(a) drawing a first medium suspected of containing an analyte into a capillary tube, where said capillary tube has bound thereto a first specific binding pair member that specifically binds the analyte, and incubating said medium and first specific binding pair member whereby a first complex involving said analyte and said first specific binding pair member is formed in relation to the presence of analyte in said first medium;
(b) expelling said first medium from said tube;
(c) drawing a second medium containing a labeled second specific binding pair member into said tube, wherein said labeled second specific binding pair member specifically binds said analyte or specifically binds a third specific binding pair member that specifically binds said analyte, where said third specific binding pair member is optionally present in said first or second medium, and incubating said labeled second specific binding pair member and said first complex, if present, to form a labeled complex;
(d) expelling said second medium from said tube;
(e) drawing a third medium containing reagents for producing a signal from said label if said label is not capable of directly producing a signal;
(f) expelling said third medium from said tube, wherein said second or said third medium, if said third medium is used, is expelled to form a pendulous drop;
(g) said pendulous drop remains outside of, but attached to said tube during examining, then examining said pendulous drop for the presence or intensity of said signal, the presence or intensity thereof being indicative of the presence or amount of analyte in said first medium.

25. The method of claim 24 wherein said analyte and specific binding pair members are each independently selected from the group consisting of ligands, receptors, and polynucleotides.

26. The method of claim 24 wherein the inner surface of said capillary tube is coated with a specific binding pair member that specifically binds said analyte.

27. The method of claim 24 wherein the inner surface of said capillary tube is coated with a receptor for a small molecule, where said small molecule is bound to a specific binding pair member that specifically binds said analyte.

28. The method of claim 27 wherein said small molecule has a molecular weight of about 150–1000.

29. The method of claim 28 wherein said small molecule is biotin and said receptor is selected from the group consisting of avidin and streptavidin.

30. The method of claim 25 wherein said labeled second specific binding pair member specifically binds said analyte.

31. The method of claim 30 wherein said labeled specific binding pair member is an antibody.

32. The method of claim 25 wherein said labeled second specific binding pair member specifically binds said third specific binding pair member, where said third specific binding pair member specifically binds said analyte.

33. The method of claim 32 wherein said third specific binding pair member is bound to a small molecule and said labeled second specific binding pair member is a labeled receptor for said small molecule.

34. The method of claim 33 wherein said small molecule is selected from the group consisting of fluorescein and fluorescein derivatives, and said labeled receptor is a labeled anti-fluorescein antibody.

35. The method of claim 24 wherein said label is able to directly produce a signal and said third medium is not used.

36. The method of claim 35 wherein said label is selected from the group consisting of fluorophors and radiolabels.

37. The method of claim 24 wherein said label is not capable of directly producing a signal.

38. The method of claim 37 wherein said label is selected from the group consisting of enzymes and chemiluminescers.

39. The method of claim 37 wherein said second medium is expelled by one or more wash solutions pushed through said capillary.

40. The method of claim 37 wherein said label is an enzyme and said third medium contains a substrate for said enzyme.

41. The method of claim 40 wherein said label is an enzyme selected from the group consisting of horseradish peroxidase, β-galactosidase, uricase and alkaline phosphatase.

42. The method of claim 24 wherein said first medium is expelled by one or more wash solutions pushed through said capillary.

43. A method of determining an analyte comprising the steps of:
 (a) drawing a first medium suspected of containing an analyte into a capillary tube, where said first medium contains a labeled analog of said analyte and where said capillary tube has bound thereto a specific binding pair member that specifically binds the analyte and the labeled analog;
 (b) expelling said first medium from said tube;
 (c) drawing a second medium containing reagents for producing a signal from said label if said label is not capable of directly producing a signal;
 (d) expelling said second medium from said tube, wherein said first or said second medium, if said second medium is used, is expelled to form a pendulous drop, and
 (e) said pendulous drop remains outside of, but attached to said tube examining, then examining said pendulous drop for the presence or intensity of said signal, the presence or intensity thereof being indicative of the presence or amount of analyte in said first medium.

44. The method of claim 43 wherein said analyte and specific binding pair member are selected from the group consisting of ligands, receptors, and polynucleotides.

45. The method of claim 43 wherein the inner surface of said capillary tube is coated with a specific binding pair member that specifically binds said analyte.

46. The method of claim 43 wherein the inner surface of said capillary tube is coated with a receptor for a small molecule, where said small molecule is bound to a specific binding pair member that specifically binds said analyte.

47. The method of claim 46 wherein said small molecule has a molecular weight of about 150–1000.

48. The method of claim 47 wherein said small molecule is biotin and said receptor is selected from the group consisting of avidin and streptavidin.

49. The method of claim 43 wherein said label is able to directly produce a signal and said third medium is not used.

50. The method of claim 49 wherein said label is selected from the group consisting of fluorophors and radiolabels.

51. The method of claim 43 wherein said label is not capable of directly producing a signal.

52. The method of claim 51 wherein said label is selected from the group consisting of enzymes and chemiluminescers.

53. The method of claim 51 wherein said first medium is expelled by one or more wash solutions pushed through said capillary.

54. The method of claim 51 wherein said label is an enzyme and said third medium contains a substrate for said enzyme.

55. The method of claim 54 wherein said label is an enzyme selected from the group consisting of horseradish peroxidase, β-galactosidase, uricase and alkaline phosphatase.

* * * * *